United States Patent [19]

Fujiwara et al.

[11] Patent Number: 5,312,999
[45] Date of Patent: May 17, 1994

[54] PROPOXYBENZENE DERIVATIVES AND PROCESS FOR PREPARING THE SAME

[75] Inventors: Toshihiro Fujiwara; Tutomu Ebata, both of Tokyo, Japan

[73] Assignee: Daiichi Seiyaku Co., Ltd., Tokyo, Japan

[21] Appl. No.: 844,543

[22] Filed: Mar. 2, 1992

Related U.S. Application Data

[62] Division of Ser. No. 290,383, Dec. 27, 1988, Pat. No. 5,136,059.

[30] Foreign Application Priority Data

| Dec. 25, 1987 | [JP] | Japan | 62-329230 |
| Dec. 28, 1987 | [JP] | Japan | 62-336489 |
| Mar. 1, 1988 | [JP] | Japan | 63-48195 |
| Mar. 31, 1988 | [JP] | Japan | 63-75968 |

[51] Int. Cl.$^5$ .............. C07C 229/02; C07C 65/01; C07C 65/10; C07C 211/44; C07C 43/225; C07C 43/23; C07C 309/19; C07C 309/20
[52] U.S. Cl. ................... 568/587; 568/585; 568/586; 549/419; 549/426; 560/9; 560/12; 560/20; 560/21; 560/23; 560/44; 560/81; 560/82; 560/106; 560/192; 560/193; 560/227; 560/250; 560/254; 562/42; 564/440; 564/442; 564/443
[58] Field of Search ............ 568/649, 586, 587, 585, 568/588; 560/9, 12, 20, 21, 23, 44, 81, 82, 106, 192, 193, 227, 250, 254; 562/42; 564/440, 442, 443; 549/419, 426

[56] References Cited

U.S. PATENT DOCUMENTS 4,393,206  7/1983  Uhrhan et al. ............ 554/51

FOREIGN PATENT DOCUMENTS 6048949  3/1985  Japan .................... 568/649

OTHER PUBLICATIONS

Iwata et al., Chem. Abstracts, vol. 107; 236723s; "Preparation of fluoropyridobenzoxazine carboxylic acids as med. bactericides" (1987).
Chemical Abstracts Formula Index, vol. 107, p. 757F, 1987.
Hayakawa et al., Chem Abstracts, vol. 101; 55108a; "Tricyclic Compounds", p. 625, 1984.

*Primary Examiner*—Marianne M. Cintins
*Assistant Examiner*—Margaret J. Page
*Attorney, Agent, or Firm*—Sughrue, Mion, Zinn, Macpeak & Seas

[57] ABSTRACT

Propoxybenzene derivatives represented by the following formula

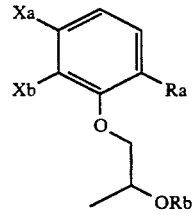

wherein Ra represents a nitro group, an amino group which may have a protecting group or an —NHCH=C(COO—$C_{1-6}$-Alkyl)$_2$ group, Rb represents a hydrogen atom, a protecting group for the hydroxyl group or a substituted sulfonyl group and Xa and Xb, which may be the same or different, each represents a halogen atom, and processes for preparation thereof are disclosed. These derivatives are useful in preparing antibacterial agents.

2 Claims, No Drawings

PROPOXYBENZENE DERIVATIVES AND PROCESS FOR PREPARING THE SAME

This is a division of application Ser. No. 07/290,383 filed Dec. 27, 1988 now U.S. Pat. No. 5,136,059.

FIELD OF THE INVENTION

This invention relates to novel propoxybenzene derivatives useful as intermediates for the synthesis of antibacterial compounds, and to a process for preparing the propoxybenzene derivatives.

BACKGROUND OF THE INVENTION

Ofloxacin, 9-fluoro-3-methyl-10-(4-methyl-1-piperazinyl) -7-oxo-2,3-dihydro-7H-pyrido[1,2,3-de][1,43-benzoxazin-6-carboxylic acid, having the following formula is knowr as disclosed in Japanese Patent 1,444,043; U.S. Pat. No. 4,382,892; and EP-B-0,047,005, as an excellent synthetic antibacterial agent and has been marketed in many countries. The 3-(S)-isomer of Ofloxacin possesses excellent potency as synthetic antimicrobial agent as disclosed in EP-A-0,206,283.

Ofloxacin

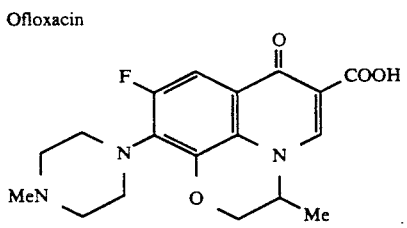

DETAILED DESCRIPTION OF THE INVENTION

The present invention relates to the propoxybenzene derivatives represented by the following formula:

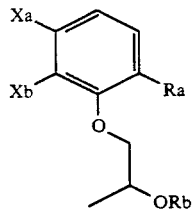

where Ra represents a nitro group, an amino group which may have a protecting group, or an —NHCH=C(COO—$C_{1-6}$-alkyl)$_2$ group, Rb represents a hydrogen atom, a protecting group for the hydroxyl gzjup or a substituted sulfonyl group, and Xa and Xb, which may be the same or different, each represents a halogen atom, such as a fluorine atom, a chlorine atom, a bromine atom, or an iodine atom, and preferably a fluorine atom.

The protecting group for the amino group can be any ordinarily known protecting groups for the amino groups, and examples thereof include acyl groups such as an acetyl group or a chloroacetyl group; aralkyl groups such as a triphenylmethyl group, a diphenylmethyl group, a benzyl group, a p-methoxybenzyl group or a p-nitrobenzyl group; alkoxycarbonyl groups such as a t-butoxycarbonyl group, a 2,2,2-trichloroethoxycarbonyl group, a benzyloxycarbonyl group, a p-methoxybenzyloxycarbonyl group or a p-nitrobenzyloxycarbonyl group; and the like.

The protecting group for the hydroxyl group can be any ordinarily known protecting groups for the hydroxyl group, and examples thereof include alkyl groups such as a t-butyl group; acyl groups such as a formyl group, an acetyl group, a trifluoroacetyl group, a benzyloxyacetyl group; ethers or alkoxyalkyl groups such as a tetrahydropyranyl group (hereinafter abbreviated as THP), a methoxymethyl group, a methoxyethoxymethyl group, a benzyloxymethyl group; aralkyl groups such as a benzyl group, a p-methoxybenzyl group, a p-nitrobenzyl group or a triphenylmethyl group, and the like.

Examples of substituted sulfonyl groups include a p-toluenesulfonyl group (hdreinafter abbreviated as a tosyl group), a methanesulfonyl group or a trifluoromethanesulfonyl group, and the like.

An object of the present invention is to provide novel compounds useful as intermediates for the synthesis of Ofloxacin and optical isomers thereof.

Another object of the present invention is to provide a novel process for preparing the intermediates used in preparing the above antimicrobial agents.

A further object of the present invention is to provide an advantageous process for the preparation of optically active intermediates for the above antimicrobial agents.

The compounds of the present invention are prepared by the following procedure.

1) Synthesis of 2,3-dihalogeno-6-nitropropoxybenzene

Among the many propoxybenzene derivatives according to the present invention, one of the most important groups of compounds are the 2,3-dihalogeno-6-nitropropoxybenzenes having the following formula (I):

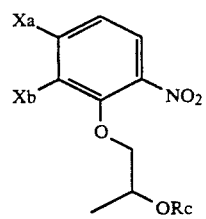

wherein Rc represents a protecting 7roup for the hydroxyl group, and Xa and Xb, which may be the same or different, each represents a halogen atom. These compounds can be obtained by reacting a 2,3,4-trihalogenonitrobenzene of the formula (II):

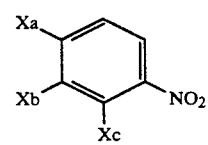

wherein Xa, Xb and Xc, which may be the same different, each represents a beloaen atom; with a 1,2-propanediol derivative of the formula (III):

(iii)

wherein Rc is as defined above; or by reacting a 2,3-dihalogeno-6-nitrophenol of the formula (IV):

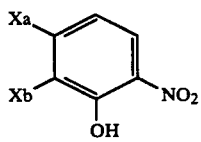

(IV)

wherein Xa and Xb are as defined above; with a compound of the formula (III) or with a compound of the formula (V):

(V)

wherein Rc is as defined above, and Xd represents a halogen atom or a sulfonyloxy group.

The compounds of formulae (II) and (IV) can be prepared according to the procedure as described in U.S. Pat. No. 4,382,892 and EP-B-0,047,005.

The reaction of 2,3,4-trihalogenonitrobenzene of the formula (II) with a compound of the formula (III) can be carried out in the presence of a base which can be either an inorganic base or an organic base. Examples of the inorganic bases include metal hydrides such as sodium hydride or calcium hydride; alkali metal hydroxides such as lithium hydroxide, sodium hydroxide, or potassium hydroxide; alkali metal carbonates such as lithium carbonate, sodium carbonate or potassium carbonate; alkali metal bicarbonates such as sodium bicarbonate or potassium bicarbonate. Examples of the organic bases include trialkylamines such as triethylamine, tri-n-butylamine, N,N-diisopropylethylamine; anilines such as N,N-dimethylaniline or N,N-diethylaniline; heterocyclic amines such as pyridine, N,N-dimethylaminopyridine or N-methylmorpholine; metal alkoxides such as sodium methoxide, sodium ethoxide, sodium isopropoxide, and potassium t-butoxide; and 1,8-diazabicyclo[5,4,0]-7undecene or N-benzyltrimethylammonium hydroxide; and the like.

The molar ratio of compound (II) to compound (III) is in the range of from about 1:1 to about 1:3, preferably 1:1.1.

The reaction is preferably carried out in the presence of a solvent inert to the reaction. Examples of such solvents include hydrocarbons such as benzene, toluene, xylene, n-hexane, cyclohexane, or n-pentane; alcohols such as methanol, ethanol, propanols and butanols; ethers such as diethyl ether, tetrahydrofuran, dioxane or 1,2-dimethoxyethane; amides such as N,N-dimethylformamide, N,N-dimethylacetamide or N-methyl-2-pyrrolidone; aprotic polar solvents such as dimethyl sulfoxide or sulforan and the like.

The reaction can be carried out at a temperature of from about $-78°$ C. to about 150° C. The reaction proceeds within the range of from 10 minutes to about 4 days.

The optically active isomer of compound of the formula (III) may be conveniently employed for the preparation of optically active propoxybenzene derivatives of the formula (I). When the optical active isomer of compound (III) is employed in this reaction, it has been confirmed that racemization of this compound did not occur and the configuration of the asymmetric carbon atom of compound (III) remained unaltered. The compound (III) was incorporated into compound (I) as the partial structure of compound (I) while retaining the original configuration of the asymmetric carbon atom of compound (III).

Another process for the preparation of compound (I) comprises reacting a 2,3-dihalogeno-6-nitrophenol of the formula (IV) with compound (III) or with compound (V). The reaction of compound (IV) with compound (iii) may preferably be achieved in the presence of Mitsunobu Reagent, which is a complex prepared by reacting an azodicarboxylic acid diester such as diethyl ester, dimethyl ester, dibenzyl ester, diisopropyl ester and the like, with triphenyl phosphine or trialkyl phosphine, as described in O. Mitsunobu, *Synthesis*, 1-28 (1981). It should be noted that the Mitsunobu Reagent is readily decomposed by moisture.

The reaction of compound (IV) with compound (III) in the presence of the Mitsunobu Reagent is preferably carried out in ethers such as diethyl ether, tetrahydrofuran, dioxane or 1,2-dimethoxyethane. The reaction can be carried out at a temperature of from about 0° C. to about 50° C.

The alternative reaction of compound (IV) with compound (V) may be carried out in the presence of a base, which can be either an inorganic or an organic base. Examples of the inorganic base include metal hydrides such as sodium hydride or calcium hydride; alkali metal hydroxides such as lithium hydroxide, sodium hydroxide, or potassium hydroxide; alkali metal carbonates such as lithium carbonate, sodium carbonate or potassium carbonate; alkali metal bicarbonates such as sodium bicarbonate or potassium bicarbonate. Examples of the organic bases include trialkylamines such as triethylamine, tri-n-butylamine or N,N-diisopropylethylamine; anilines such as N,N-dimethylaniline or N,N-diethylaniline; heterocyclic amines such as pyridine, N,N-dimethylaminopyridine or N-methylmorpholine; metal alkoxides such as sodium methoxide, sodium ethoxide, sodium isopropoxide, and potassium tert-butoxide; 1,8-diazabicyclo[5,4,0]-7-undecene or N-benzyltrimethylammonium hydroxide and the like. The reaction can be carried out in the presence of a solvent inert to the reaction. Examples of the solvents include hydrocarbons such as benzene, toluene, xylene, n-hexane, cyclohexane, or n-pentane; alcohols such as methanol, ethanol, propanols and butanols; ethers such as diethyl ether, tetrahydrofuran, dioxane or 1,2-dimethoxyethane; amides such as N,N-dimethylformamide, N,N-dimethylacetamide or N-methyl-2-pyrrolidone; aprotic polar solvents such as dimethyl sulfoxide or sulforan and the like. The reaction can be carried out at the temperature of from room temperature to a boiling point of the solvent employed. The reaction may be accelerated by adding potassium iodide, sodium iodide or crown ether to the reaction mixture. The amount of such an accelerating reagent can be in the range of from 1/100 to 1 molar equivalent to compound (IV).

The compound (III), a derivative of 1,2-propanediol, can be obtained by reducing a derivative of lactic acid or lactic acid ester. The hydroxyl group of lactic acid derivative should be protected in a suitable form prior to the reduction. Examples of such protecting group include a tetrahydropyranyl group, a benzyl group, a p-methoxybenzyl group, a methoxymethyl group or a triphenylmethyl group, and the like. The protected lactic acid derivative is then reduced with a metal hydride such as lithium aluminum hydride and sodium borohydride, etc. to yield a protected 1,2-propanediol derivative (III). This compound can be converted to a sulfonyloxy compound or a halide (compound (V)) by the known method such as that using a sulfonyl chloride in the presence of a base or thionyl chloride, and the like.

As is apparent from the structure of lactic acid, it has an asymmetric carbon atom. The pure optical isomer and racemic mixture of both lactic acid or lactic acid esters are commercially available. Thus, either optically pure or racemic propoxybenzene derivative (I) is easily prepared according to the present invention.

As shown in the following reaction scheme, the compound (I) can be converted to benzoxazine compound (XV) by a series of reactions such as a) reduction of nitro group, b) methylenemalonation of amino group, c) removal of the protecting group of hydroxyl group, d) sulfonylation of the hydroxyl group, and e) cyclization.

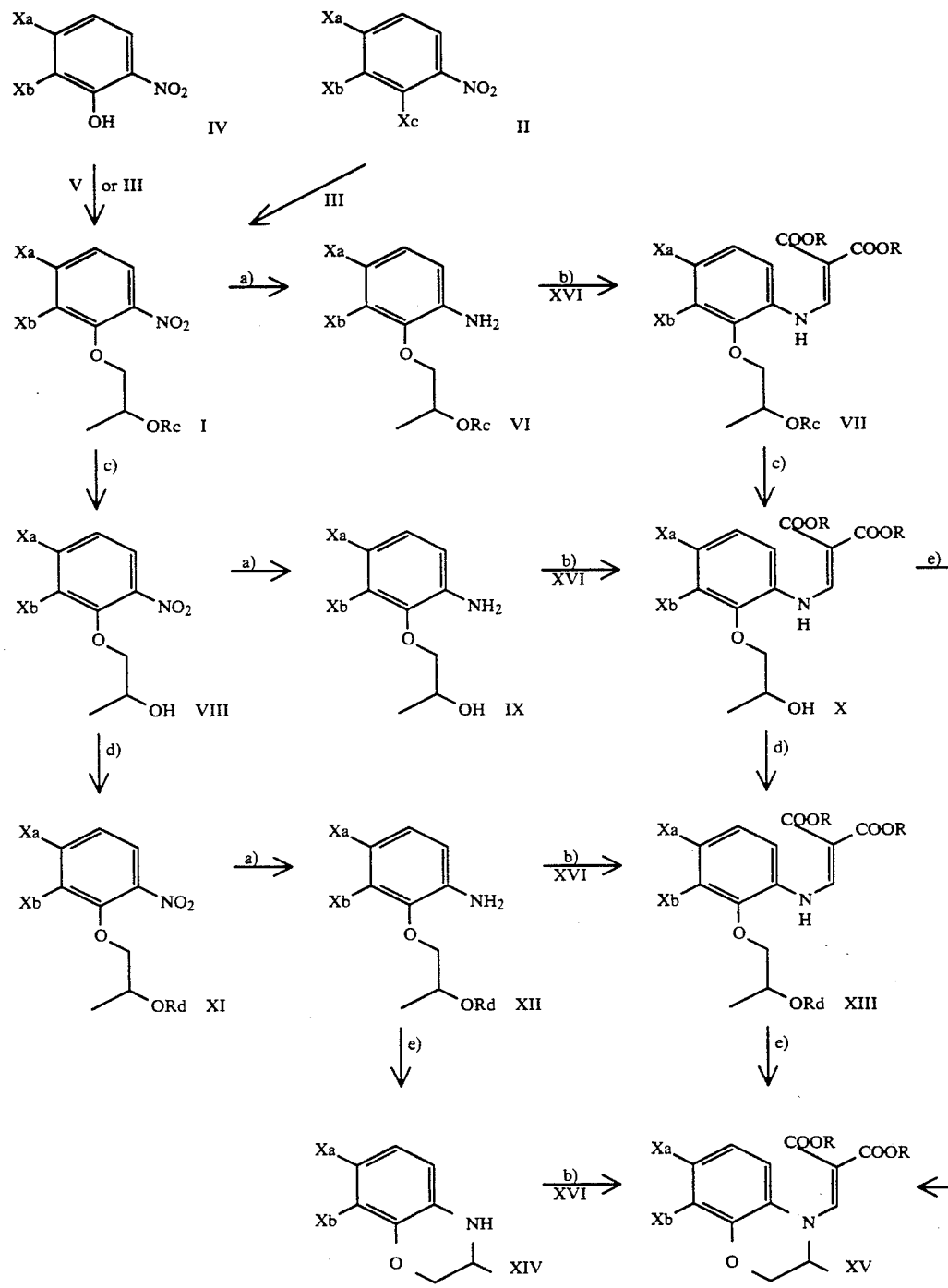

III: $HOCH_2CH(CH_3)ORc$
V: $X_aCH_2CH(CH_3)ORc$
XVI: $Y-CH=C(COOR)_2$ $R_d$: substituted sulfonyl group
R: $-CH_2CH_3$ or $-CH_3$ In the series of reactions, the product obtained in each reaction can be isolated or purified by known methods such as extraction, recrystallization or chromatography over silica gel or a combination thereof.

Each of the reactions in the reaction scheme (I) to (XV) is described hereinafter in detail.

Step a): Reduction of Nitro Group

The reduction of nitro group in compound (I) may be achieved by catalytic reduction using a catalyst such as Raney nickel, palladium on charcoal and platinum oxide and the like, with hydrosulfite or with combined reagent of sodium borohydride and metal chlorides. Examples of the solvent which can be used for these reductions include lower alcohols such as methanol, ethanol and propanols. The reduction can be accomplished at a temperature of from room temperature to the boiling point of the solvent. Catalytic reduction can be accomplished under atmospheric or pressurized hydrogen atmosphere.

The amino group may be protected by introducing a suitable protecting group such as acetyl group (by the reaction of acetyl chloride or acetic anhydride), triphenylmethyl group (by the reaction of triphenylmethyl chloride), tert-butoxycarbonyl group (by the reaction of di-t-butyl dicarbonate) or benzyloxycarbonyl group (by the reaction of benzyloxycarbonyl chloride). The removal of the protecting group can be accomplished by the known methods suitable per se.

Step b): Methylenemalonylation of the Amino Group

The methylenemalonylation reaction of the amino group can be accomplished by reacting the amino compound such as compound (VI), (IX) or (XII) with a compound of the following formula (XVI)

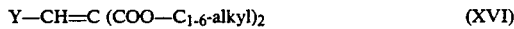

$$Y-CH=C(COO-C_{1-6}\text{-alkyl})_2 \quad (XVI)$$

wherein Y represents an alkoxyl group, a halogen atom or a dialkylamino group having from 1 to 6 carbon atoms in each of the alkyl moieties; in the presence or absence of a solvent.

The amount of compound (XVI) is suitably more than equimolar to the amino compound.

The solvent used for the reaction can be any inert solvent. Examples of the solvents include hydrocarbons such as benzene, toluene, xylene, n-hexane, cyclohexane, or n-pentane; alcohols such as methanol, ethanol, propanols and butanols; ethers such as diethyl ether, tetrahydrofuran, dioxane or 1,2-dimethoxyethane; amides such as N,N-dimethylformamide, N,N-dimethylacetamide or N-methyl-2-pyrrolidone; aprotic polar solvents such as dimethyl sulfoxide or sulforan, and the like.

The reaction can be accomplished at a temperature of from about 100° C. to about 180° C. when the reaction is carried out in the absence of the solvent. when a solvent is employed, the reaction can be suitably achieved at the boiling point of the solvent.

Step c): Removal of the Protecting Group of Hydroxyl Group

The removal of the protecting group of hydroxyl group is accomplished in a conventional manner known per se. For example, removal of THP group is accomplished by treating the protected compounds in an acidic condition at a temperature of from room temperature to 100° C. Examples of the acidic condition include a treatment with hydrogen chloride, hydrogen bromide or sulfuric acid in an alcohol or with pyridinium p-toluenesulfonate in a protolytic solvent, such as a lower alcohol, water, a carboxylic acid, e.g., acetic acid.

Step d): Sulfonylation of Hydroxyl Group

The sulfonylation reaction can be accomplisher by reacting a substituted sulfonyl halide such as p-toluenesulfonyl chloride, methanesulfonyl chloride or trifluoromethanesulfonyl anhydride in the presence of a base with the deprotected hydroxy compound. Examples of such bases include trialkylamine such as triethylamine, tri-n-butylamine, N,N-diisopropylethylamine; anilines such as N,N-dimethylaniline or N,N-diethylaniline; heterocyclic amines such as pyridine, N,N-dimethylaminopyridine or N-methylmorpholine; and 1,8-diazabicyclo-5,4,0]-7-undecene, and the like.

An aprotic solvent is suitably employed for the reaction, and examples thereof include ethers such as tetrahydrofuran, dioxane, 1,2-dimethoxyethane or diethyl ether and the like; amides such as dimethylformamide, N,N-dimethylacetamide or N-methyl-2-pyrrolidone and the like; halogenated hydrocarbons such as dichloromethane, chloroform or 1,2-dichloroethane and the like.

Step e): Cyclization to Benzoxazine Derivatives

Some of the compounds of the present invention can be cyclized to the known benzoxazine derivatives represented by formulae (XIV) and (XV).

The sulfonyloxy compounds of formula (XII) or (XIII) can be cyclized to the benzoxazine derivative under a basic condition. Either inorganic or organic base can be employed in the cyclization of the sulfonyloxy compounds. Examples of inorganic bases which can be used include alkali metal hydroxides such as lithium hydroxide, sodium hydroxide, or potassium hydroxide; alkali metal carbonates such as lithium carbonate, sodium carbonate or potassium carbonate; alkali metal bicarbonates such as sodium bicarbonate or potassium bicarbonate. Examples of the organic bases which can be used include trialkylamines such as triethylamine, tri-n-butylamine, N,N-diisopropylethylamine; anilines such as N,N-dimethylaniline or N,N-diethylaniline; heterocyclic amines such as pyridine, N,N-dimethylaminopyridine or N-methylmorpholine; metal alkoxides such as sodium methoxide, sodium ethoxide, sodium isopropoxide, and potassium t-butoxide; 1,8-diazabicyclo[5,4,0]-7-undecene or N-benzyltrimethylammonium hydroxide and the like.

The cyclization can be achieved at a temperature of from about room temperature to about 150° C. in a solvent. Examples of the solvents include alcohols such as methanol, ethanol, propanols or butanols; ethers such as diethyl ether, tetrahydrofuran, dioxane, 1,2-dimethoxyethane, 2-methoxyethyl ether or ethylene glycol diethyl ether and the like; amides such as N,N-dimethylformamide, N,N-dimethylacetamide or N-methyl-2-pyrrolidone and the like; aprotic polar solvents such as dimethyl sulfoxide or sulforan and the like.

The cyclization reaction may be accelerated by adding potassium iodide, sodium iodide or crown ether to the reaction mixture. The amount of such accelerating reagent may be preferably 1/20 molar equivalent or more to the propoxybenzene derivative.

The cyclization of the hydroxy compound of formula (X) can be effected after the compound is converted to a halide thereof with a halogenating agent such as thionyl chloride, phosphorous trichloride or phosphorous tribromide and the like. The cyclization can be achieved in the presence of the same base as exemplified for the cyclization of the sulfonyloxy compounds of formulae (XII) and (XIII).

The hydroxy compound can also be cyclized to a benzoxazine derivative by reacting from 1 to 1.5 molar equivalent of Mitsunobu Reagent in ethers such as diethyl ether, tetrahydrofuran, or 1,2-dimethoxyethane at a temperature of from about 0° C. to about 50° C.

The cyclization of the propoxybenzene compound to the benzoxazine compound accompanies the inversion of the configuration at the asymmetric carbon atom in the propoxy moiety. Thus, the 3-(S)-alkyl benzoxazine derivatives are obtained by cyclization of the (R)-propoxybenzene derivatives; and the 3-(R)-benzoxazine derivatives are obtained frcm the (S)-propoxybenzene derivatives.

The compounds of formulae (XIV) and (XV) can te converted into Ofloxacin by the method as described in U.S. Pat. No. 4,382,892 or EP-B-0,047,005. Also, an optical isomer of the compounds of formulae (XIV) and (XV) can be converted into an optical isomer of Ofloxacin by the method as described in EP-A-0,206,283.

This invention is illustrated in greater detail with reference to the following examples, but it should be understood that they are not intended to limit the present invention.

REFERENCE EXAMPLE A-1

(1) O-(Tetrahydropyran-2-yl)lactic acid ethyl ester

In 125 ml of anhydrous diethyl ether, 29.53 g of dl-ethyl lactate, 25.54 g of 2,3-dihydropyran and 2.9 g of dl-camphor-10-sulfonic acid were dissolved under cooling with ice. The mixture was stirred at room temperature overnight. To the mixture was added 150 ml of diethyl ether, and the ethereal solution was washed successively with a saturated sodium bicarbonate aqueous solution, water, and a saturated sodium chloride aqueous solution. The organic layer was dried over anhydrous magnesium sulfate. The solvent was removed under reduced pressure to yield the titled compound in quantitative yield.

(2) 2-0-(Tetrahydropyran-2-yl)propane-1 2-diol (III, Rc=THP)

To a suspension of 10.04 g of lithium aluminum hydride in 500 ml of anhydrous diethyl ether, a solution of 52 g of the ester obtained in the Reference Example A-1 (1) in 150 ml of anhydrous diethyl ether was added with stirring under cooling with ice. The mixture was stirred at room temperature for 20 minutes, then heated under refluxing for 2 hours and stirred again at room temperature overnight. The mixture was externally cooled with ice, and to this mixture were added sequentially 10.04 ml of water, 10.04 ml of a 15% sodium hydroxide aqueous solution, and 30.12 ml of water in the order indicated with stirring. Resulting insoluble material was removed by filtration, and the filtrate was concentrated to about a half of the original volume. The condensate was dried over anhydrous magnesium sulfate. The solvent was removed under reduced pressure to yield the titled compound in quantitative yield. This product was purified by distillation under reduced pressure.

b.p.: 108°–114° C. (14 mm Hg), $^1$H-NMR (CDCl$_3$) δ: 1.13, 1.22 (totally 3H, d each, J=6.5 Hz), 1.30–1.94 (6H, m), 2.28 (1H, dd, J=5.5 and 7 Hz), 3.26–4.10 (5H, m), 4.48–4.78 (1H, m)

These two examples were achieved according to the method described in *J. Am. Chem Soc.*, 106, 4916–4922 (1984).

EXAMPLE 1

2,3-Difluoro-6-nitro-{[2-(tetrahydropyran-2-yl)-oxy-propyl]oxy}benzene (I, Xa=Xb=F, Rc=THP)

To a solution of 2.04 g of triphenylphosphine in 10 ml of anhydrous tetrahydrofuran was added dropwise 1.36 g of diethyl azodicarboxylate with stirring under cooling with ice, and the resulting mixture was stirred at the same temperature for 30 minutes. To this solution was added dropwise a solution of 1.05 g of 2,3-difluoro-6-nitrophenol (IV, Xa=Xb=F), 1.01 g of 2-0-(tetrahydropyran-2-yl)propane-1,2-diol (III, Rc=THP) in 5 ml of anhydrous tetrahydrofuran and then the mixture was stirred at room temperature overnight. The solvent was removed under reduced pressure, and to the residue was added benzene and a saturated sodium bicarbonate aqueous solution. After the mixture was shaken, the organic layer was separated and washed successively with water and a saturated sodium chloride aqueous solution. The organic layer was dried over anhydrous magnesium sulfate, and then the solvent was removed under reduced pressure. The residue was purified through silica gel column to yield 1.85 g of the titled compound.

This product contained the diastereoisomeric isomers, and each diastereomer was observed as a different spot on TLC. The $^1$H-NMR spectrum of the product detected as the major spot on TLC, one of the two spots, was as indicated below. The $^1$H-NMR spectrum of the product detected as the minor spot on TLC was almost identical to that of the major one.

$^1$H-NMR (CDCl$_3$) δ: 1.18–1.84 (9H, m), 3.23–4.28 (5H, m), 4.74 (1H, br s), 6.94 (1H, ddd, J=5, 7.5, 9 Hz), 7.65 (1H, ddd, i=2.5, 5, 9 Hz)

EXAMPLE 2

2,3-Difluoro-6-amino-{[2-(tetrahydropyran-2-yl)oxy-propyl]oxy}benzene (VI, Xa=Xb=F, Rc=THP)

To a solution of 1.82 g of the compound obtained in Example 1 dissolved in 50 ml of ethanol was added 500 mg of 5% palladium on charcoal. Catalytic reduction was carried out under atmospheric pressure for about 1 hour. The catalyst was removed by filtration, and the solvent was removed under reduced pressure to yield the titled compound. This product was used in the next step without further purification.

EXAMPLE 3

2,3-Difluoro-6-(2,2-diethoxycarbonylethenyl)amino-[2-(hydroxypropyl)oxy]benzene (X, Xa=Xb=F, R=Et)

To the total amount of the product obtained in Example 2 was added 1.24 g of diethyl ethoxymethylenemalonate (XVI, Y=EtO, alkyl=Et, hereinafter abbreviated as EMME). The mixture was heated to 145° to 150° C. with stirring. After 1.5 hours, the system was evacuated to remove formed ethanol, and the mixture was heated a further 30 minutes with stirring under reduced pressure. After cooling, the product was isolated through silica gel column chromatography to yield 1.33 g of the titled compound, which has no tetrahydropyranyl moiety.

A minor product having tetrahydropyranyl moiety, weighing 580 mg, was also obtained. This compound was converted to the titled compound by the treatment with pyridinium tosylate.

m.p.: 52°–55° C., MS; m/e=373 (M+)

$^1$H-NMR (CDCl$_3$) δ: 1.22–1.46 (9H, m), 3.55 (1H, d, J=4.5 Hz), 3.88–4.43 (7H, m), 6.75–7.08 (2H, m), 8.48 (1H, d, J=14.5 Hz)

REFERENCE EXAMPLE B-1

Diethyl (7,8-difluoro-3-methyl-3,4-dihydro-2H-[1,4]benzoxazine-4-yl)methylenemalonate (XV, Xa=Xb=F, R=Et)

To a solution of 341 mg of triphenylphosphine in 5 ml of anhydrous tetrahydrofuran was added dropwise 226 mg of diethyl azodicarboxylate and the mixture was stirred under cooling with ice for 20 minutes. To this solution was added a solution of 373 mg of the compound obtained in Example 3 in 3 ml of anhydrous tetrahydrofuran, and the mixture was stirred at room temperature overnight.

The solvent was removed under reduced pressure, the residue was purified through silica gel column chromatography to yield the titled compound in quantitative yield. This product was identical to an authentic sample (obtained as described in JP-A-85-126190) (the term "JP-A" as used herein refers to a "published unexamined Japanese patent application") in physical property.

m.p.: 68° C.

$^1$H-NMR (CDCl$_3$) δ: 1.20–1.41 (9H, m), 3.90–4.44 (7H, m), 6.71–6.85 (2H, M), 7.76 (1H, s)

EXAMPLE 4

2,3-Difluoro-6-(2,2-diethoxycarbonylethenyl)amino-[(2-p-toluenesulfonyloxypropyl)oxy]benzene (XIII, Xa=Xb=F, Rd=Ts, R=Et)

To a solution of 747 mg of the compound obtained in Example 3 in 2 ml of pyridine was added 710 mg of p-toluenesulfonyl chloride and the mixture was stirred under cooling with ice for 24 hours, and then at room temperature for 4 hours. To the mixture were added ethyl acetate and 1 N hydrochloric acid. The mixture was shaken, and the organic layer was separated. The organic layer was washed with water and dried over anhydrous magnesium sulfate. The solvent was removed under reduced pressure. The residue was purified through silica gel column chromatography to yield 1.0 g of the titled compound.

m.p.: 61°–62° C.

$^1$H-NMR (CDCl$_3$) δ: 1.34, 1.36 (3H each, t each, J=7 Hz), 1.50 (3H, d, J=7 Hz), 2.40 (3H, s), 4.12–4.40 (6H, m), 4.94 (1H, sixtet-like), 6.83–6.97 (2H, m), 7.26, 7.76 (2H each, d each, J=9 Hz), 8.34 (1H, d, J=14 Hz)

REFERENCE EXAMPLE C-1

Diethyl (7,8-difluoro-3-methyl-3,4-dihydro-2H-[1,4]benzoxazine-4-yl)methylenemalonate (XV, Xa=Xb=F, R=Et)

To a solution of 791 mg of the compound obtained in Example 4 in 5 ml of anhydrous N,N-dimethylformamide (hereinafter abbreviated as DMF), 207 mg of potassium carbonate and a catalytic amount of 18-crown-6-ether were added, and the mixture was heated at 80° C. for 8.5 hours. To the mixture were added ethyl acetate and water. The mixture was shaken, and the organic layer was separated. The organic layer was washed with water and dried over anhydrous magnesium sulfate. The solvent was removed under reduced pressure. The residue was purified through silica gel column chromatography to yield the titled compound as crystals in quantitative yield. The physical data of the product were identical to those of the authentic specimen as described in Reference Example B-1.

EXAMPLE 5

2,3-Difluoro-6-nitro-[(2-hydroxypropyl)oxy]benzene (VIII, Xa=Xb=F)

A mixture of 6.35 g of 2,3-difluoro-6-nitro-{[2-(tetrahydropyran-2-yl)oxypropyl]oxy}benzene (I, Xa=Xb=F, Rc=THP), 60 ml of anhydrous ethanol and 640 mg of pyridinium tosylate was stirred at room temperature overnight and then heated under refluxing for 1 hour. The solvent was removed under reduced pressure. To the residue were added ethyl acetate and 1 N hydrochloric acid. The mixture was shaken, and the organic layer was separated. The organic layer was washed successively with a saturated sodium bicarbonate aqueous solution and water, then dried over anhydrous magnesium sulfate. The solvent was removed under reduced pressure to yield the oily titled compound. This product was used in the following reaction without purification.

$^1$H-NMR (CDCl$_3$) δ: 1.25 (3H, d, J=6 Hz), 3.00 (1H, br d, J=2.5 Hz), 3.99–4.43 (3H, m), 7.03 (1H, ddd, J=7, 9, 9.5 Hz), 7.74 (1H, ddd, J=2.5, 5.5, 7 Hz)

EXAMPLE 6

2,3-Difluoro-6-(2,2-dimethoxycarbonylethenyl)amino-[(2-hydroxypropyl)oxy]benzene (X, Xa=Xb=F, R=Me)

To a solution of 3.17 g of the compound obtained in Example 5 in 45 ml of ethanol was added 780 mg of 5% palladium on charcoal, and the catalytic reduction was carried out under atmospheric pressure at room temperature. The catalyst was removed by filtration and the solvent was removed under reduced pressure. To the residue was added 2.44 g of dimethyl methoxymethylenemalonate (XVI, Y=OMe, alkyl=Me), and the mixture was heated at 140° C. with stirring as follows: under atmospheric pressure for 1 hour; then under reduced pressure for 1 hour; and then under atmospheric pressure for 1 hour. After cooling, the mixture was purified through silica gel column chromatography to yield 4.0 g of the titled compound.

m.p.: 107°–108° C.

$^1$H-NMR (CDCl$_3$) δ: 1.29 (3H, d, J=6.5 Hz), 3.45 (1H, d, J=4.5 Hz), 3.80, 3.88 (3H each, s each), 6.76–7.12 (2H, m), 8.53 (1H, J=14.5 Hz)

EXAMPLE 7

2,3-Difluoro-6-(2,2-dimethoxycarbonylethenyl)amino-[(2-p-toluenesulfonyloxypropyl)oxy]benzene (XIII, Xa=Xb=F, Rd=Ts, R=Me)

To a solution of 2.07 g of the compound obtained in Example 6 in 4.2 ml of pyridine was added 1.49 g of p-toluenesulfonyl chloride and the mixture was stirred at an external temperature of 5° C. for 3 days. To the mixture was added ethyl acetate, and the solution was washed successively with 1 N hydrochloric acid, a saturated sodium bicarbonate aqueous solution and water, and then dried over anhydrous magnesium sulfate. The solvent was removed under reduced pressure. The residue was purified through silica gel column chromatography to yield 2.76 g of the titled compound.

m.p.: 89°–90° C.

$^1$H-NMR (CDCl$_3$)δ: 1.50 (3H, d, J=6.5 Hz), 2.40 (3H, s), 3.80, 3.85 (3H each, s each), 4.04–4.42 (2H, M), 4.80–5.14 (1H, m), 6.76–7.12 (2H, m), 7.28, 7.80 (2H each, d each, J=8 Hz), 8.41 (1H, J=14 Hz)

REFERENCE EXAMPLE C-2

Dimethyl (7,8-difluoro-3-methyl-3,4-dihydro-2H-[1,4]benzoxazine-4-yl)methylenemalonate (XV, Xa=Xb=F, R=Me)

A mixture of 749 mg of the compound obtained in Example 7, 207 mg of potassium carbonate and 5 ml of anhydrous DXF was heated at 80° C. for 8 hours. The mixture was diluted with ethyl acetate, and the resulting mixture was washed with water and dried over anhydrous magnesium sulfate. The solvent was removed under reduced pressure. The residue was purified through silica gel column chromatography to yield 455 mg of the titled compound.

m.p.: 146°–147° C.

$^1$H-NMR (CDCl$_3$) δ: 1.32 (3H, d, J=7 Hz), 3.81, 3.85 (3H each, s each), 3.94–4.63 (3H, m), 4.80–5.14 (1H, m), 6.80 (2H, q-like m), 7.82 (1H, s)

EXAMPLE 8

2,3-Difluoro-6-nitro-(2-p-toluenesulfonyloxypropyl)oxybenzene XI, Xa=Xb=F, Rd=Ts)

To a solution of 4.5 g of the compound obtained in Example 5 in 8.6 ml of pyridine was added 4.36 g of p-toluenesulfonyl chloride and the mixture was stirred under cooling with ice for 4 hours, and then at room temperature for 4 hours. To the mixture were added ethyl acetate and 1 N hydrochloric acid. The mixture was shaken, and the organic layer was separated. The organic layer was washed with water and dried over anhydrous magnesium sulfate. The solvent was removed under reduced pressure. The residue was purified through silica gel column chromatography to yield 6.52 g of the titled compound.

m.p.: 67°–69° C.

$^1$H-NMR (CDCl$_3$) δ: 1.44 (3H, d, J 6 Hz), 2.41 (3H, s), 4.08–4.40 (2H, m), 4.76–5.08 (1H, m), 7.30 (1H, sixtet-like), 7.67 (1H, ddd, J=2.5, 5.5, 8.5 Hz), 7.32, 7.80 (2H each, d each, J=8 Hz)

EXAMPLE 9

2,3-Difluoro-6-amino-[(2-p-toluenesulfonyloypropyl)oxy]benzene (XII, Xa=Xb=F, Rd=Ts)

To a solution of 2.32 g of the compound obtained in Example 8 in 50 ml of ethanol was added 1 g of 5% palladium on charcoal, and the catalytic reduction was carried out under atmospheric pressure at room temperature for about 1 hour. The catalyst was removed by filtration, and the solvent was removed under reduced pressure to yield the titled compound. This product was used in the following reaction without purification.

EXAMPLE 10

2,3-Difluoro-6-(2,2-diethoxycarbonylethenyl)amino-[(2-p-toluenesulfonyloxxypropyl)oxy]benzene (XIII, Xa=Xb=F, Rd=Ts, R=Et)

A mixture of the total amoun obtained in Example 9 and 1.30 g of EKKE was heated at 140° to 150° C. with stirring as follows: under atmospheric pressure for 1 hour; then under reduced pressure for 1 hour. The reaction mixture was purified through silica gel column chromatography to yield 1.64 g of the titled compound. This compound was identical to that obtained in Example 3.

REFERENCE EXMPLE D-1

7,8-Difluoro-3-methyl-3,4-dihydro-2H-[1,4]benzoxazine (XIV, Xa=Xb=F)

To a solution of 720 mg of the compound obtained in the same manner as in Example 9 in 5 ml of DMF were added 276 mg of potassiam carbonate and catalytic amount of 18-crown-6-ether. The mixture was heated at 80° C. overnight. To the mixture were added ethyl acetate and water. The mixture was shaken, and the organic layer was separated. The organic layer was washed with water and dried over anhydrous magnesium sulfate. The solvent was removed under reduced pressure. The residue was purified through silica gel column chromatography to yield 267 mg of the titled compound. The physical data of the product were identical to those of the authentic specimen obtained as described in U.S. Pat. No. 4,382,892 and EP-B-0,047,005.

m.p.: 52° C. (identical to that of the authentic compound)

REFERENCE EXAMPLE A-2

(1)(S)-Ethyl-O-(tetrahydropyran-2-yl)lactate

A mixture of 50.06 g of (S)-(−)-ethyl lactate, 50.48 g of 2,3-dihydropyran, 5.8 g of dl-camphor-10-sulfonic acid and 250 ml of anhydrous diethyl ether was stirred under cooling with ice for 30 minutes and then at room tempe rature overnight. To the mixture was added 300 ml of diethyl ether and the ethereal solution was washed successively with a saturated sodium bicarbonate aqueous solution and a saturated sodium chloride aqueous solution. The resulting solution was dried over anhydrous magnesium sulfate. The solvent was removed under reduced pressure to yield the titled compound in quantitative yield.

(2) 2-O -(Tetrahydropyran-2-yl)-(S)-propane-1,2-diol (IIIS, Rc=THP)

To a suspension of 20.1 g of lithium aluminum hydride in 1,000 ml of anhydrous diethyl ether, a solution of the total amount of the ester obtained in Reference Example A-2 (1) in 200 ml of anhydrous diethyl ether was added dropwise with stirring under cooling with ice. The mixture was stirred at room temperature for 1 hour, then heated under ref lux for 2 hours and again at room temperature overnight. The mixture was externally cooled with ice and to the mixture were added 20.1 ml of water, 20.1 ml of a 15% sodium hydroxide aqueous solution, 61.5 ml of water in the order indicated with stirring. The resulting insoluble material was removed by filtration, the filtrate was dried over anhydrous magnesium sulfate. The solvent was removed under reduced pressure. The residue was distilled under reduced pressure to yield the titled compound as a mixture of diastereomers.

b.p.: 88°–93° C. (5 Mm Hg)

$^1$H-NMR (CDCl$_3$) δ: 1.13 and 1.22 (3H totally, d each, J=6.5 Hz), 1.36–1.96 (6H, m), 3.30–4.12 (5H, m), 4.50–4.60, 4.68–4.80 (1H, m)

EXAMPLE 11

2,3-Difluoro-6-nitro-{[(S)-2-(tetrahydropyran-2-yl)oxypropyl]oxy}benzene (IS, Xa=Xb=F, Rc=THP)

The titled compound was obtained as an oily product, according to the method as described in Example 1, starting from 12.26 g of 2,3-difluoro-6-nitrophenol (IV, Xa=Xb=F), 11.78 g of 2-O-(tetrahydropyran-2-yl)-(S)-propane-1,2-diol (IIIS, Rc=THP) and 1.3 molar equivalent (to the phenol) of Mitsunobu Reagent. The product, weighing 20.4 g, was a mixture of the diastereomers.

$^1$H-NMR (CDCl$_3$) δ: 1.28, 1.32 (3H totally, d each, J=6 Hz), 1.40–1.86 (6H, m), 3.36–4.42 (5H, m), 4.63–4.86 (1H, m), 7.00 (1H, ddd, J=7, 9, 9.5 Hz), 7.68 (1H, ddd, J=2.5, 5, 9 Hz)

EXAMPLE 12

2,3-Difluoro-6-nitro-{[(S)-(2-hydroxypropyl)]oxy}benzene (VIIIS, Xa=Xb=F)

The removal of tetrahydropyranyl group was achieved from 6.35 g of the product obtained in Example 11 and 640 mg of pyridinium tosylate according to the method as described in Example 5. An oily product was obtained, and the product was used in the following reaction without purification.

$^1$H-NMR (CDCl$_3$) δ: 1.26 (3H, d, J=6 Hz), 2.88 (1H, d, J=2.5 Hz), 3.96–4.44 (3H, m), 7.03 (1H, ddd, J=7, 9, 9.5 Hz), 7.75 (1H, ddd, J=2.5, 5.5, 7 Hz)

EXAMPLE 13

2,3-Difluoro-6-nitro-{[(S)-(2-p-toluenesulfonyloxypropyl)]oxy}benzene (XIS, Xa=Xb=F, Rd=Ts)

According to the tosylating method as described in Example 8, 6.98 g of the titled compound was obtained from 4.35 g of the compound obtained in Example 12. m.p.: 68°–69.5° C.

$^1$H-NMR (CDCl$_3$) δ: 1.44 (3H, d, J=6 Hz), 2.42 (3H, S), 4.08–4.40 (2H, M), 4.76–5.08 (1H, ddd, J=7, 9, 9.5 Hz), 7.68 (1H, ddd, J=2.5, 5.5, 7 Hz)

EXAMPLE 14 AND REFERENCE EXAMPLE D-2

(R)-(+)-7,8-Difluoro-3,4-dihydro-3-methyl-2H-[1,4]-benzoxazine (XIVR, Xa=Xb=F)

According to the methods described in EXample 9 and Reference Example D-1, 280 mg of the titled compound was obtained from 775 mg of 2,3-difluoro-6-nitro{[(S)-2-p-toluenesulfonyloxypropyl]oxy}benzene (XIVR, Xa=Xb=F, Rd=Ts). The product was identical to the authentic specimen (obtained as described in *Agric. Biol. Chem.*, 51, (5), 1265-1270 (1 987) ) in the physical data.

REFERENCE EXAMPLE A-3

(1) (R)-Methyl-O-(tetrahydropyran-2-yl)lactate

A mixture of 31.23 g of (R)-(+)-methyl lactate (available from DAISEL CHEMICAL INDUSTRIES, LTD.), 30.28 g of 2,3-dihydropyran, 3.48 g of dl-camphor-10-sulfonic acid and 150 ml of anhydrous diethyl ether was stirred under cooling with ice for 30 minutes and then at room temperature overnight. To the mixture was added 300 ml of diethyl ether, and the resulting ethereal solution was washed with a saturated sodium bicarbonate aqueous solution, water and a saturated sodium chloride aqueous solution. The organic layer was dried over anhydrous magnesium sulfate. The solvent was removed under reduced pressure to yield the oily titled compound in quantitative yield.

$^1$H-NMR (CDCl$_3$) δ: 1.20, 1.26 (3H totally, d, J=6.5 Hz), 1.36–2.02 (6H, m), 3.74 (3H, s), 3.32–4.02 (2H, m), 4.22, 4.44 (1H totally, q each, J=7 Hz), 4.64–4.78, 4.90–5.02 (1H totally, m)

(2) 2-O-(Tetrahydropyran-2-yl)-(R)-propane-1,2-diol (IIIR, R=THP)

To a suspension of 25.7 g of lithium aluminum hydride in 800 ml of anhydrous diethyl ether, a solution of 57.09 g of the compound obtained in Reference Example A-3 (1) in 200 ml of anhydrous diethyl ether was added dropwise with stirring under cooling with ice. The mixture was stirred at room temperature for 1 hour, then heated under reflux for 2 hours and left at room temperature overnight. The mixture was cooled with ice externally, and to this were added 25.7 ml of water, 25.7 ml of 15% sodium hydroxide aqueous solution, and 77.1 ml of water successively with stirring. An insoluble material was removed by filtration, and the filtrate was dried over anhydrous magnesium sulfate. The solvent was removed under reduced pressure, and the residue was distilled under reduced pressure to yield the titled compound as a mixture of diastereomers.

b.p.: 86°–90.5° C. (4.5–5 mm Hg), 40.21 g.

$^1$H-NMR (CDCl$_3$) δ: 1.13, 1.22 (3H totally, d each, J=6.5 Hz), 1.33–1.97 (6H, m), 2.21 (1H, t-like, J=5.5 Hz), 3.28–4.13 (5H, m), 4.48–4.81 (1H, m)

EXAMPLE 15

2,3-Difluoro-6-nitro-{[(R)-2-(tetrahydropyran-2-yl)oxypropyl]oxy}benzene (IR, Xa=Xb=F, R=THP)

The oily titled compound was obtained according to the method as described in Example 1 from 12.21 g of 2,3-difluoro-6-nitrophenol (IV, Xa=Xb=F), 11.76 g of 2-O-(tetrahydropyran-2-yl)-(R)-propane-1,2-diol (IIIR, Rc=THP) and 1.3 molar equivalent (to the phenol) of Mitsunobu Reagent. The yield of the product weighed 20.49 g.

$^1$H-NMR (CDCl$_3$) δ: 1.28, 1.32 (3H totally, d each, J=6 Hz), 1.40–1.94 (6H, m), 3.34–4.44 (5H, m), 4.68–4.86 (1H, m), 7.00 (1H, ddd, J 7, 9, 9.5 Hz), 7.68 (1H, ddd, J=2.5, 5, 9 Hz)

EXAMPLE 16

2,3-Difluoro-6-nitro-{[(R)-(2-hydroxypropyl)]oxy}benzene (VIIIR, Xa=Xb=F)

According to the method as described in Example 5, 4.62 g of the oily titled compound was obtained from 6.35 g of the compound obtained in Example 15.

$^1$H-NMR (CDCl$_3$) δ: 1.26 (3H, d, J=6 Hz), 2.89 (1H, d, J=2.5 Hz), 3.95–4.46 (3H, M), 7.03 (1H, ddd, J=7, 9, 9.5 Hz), 7.75 (1H, ddd, J=2.5, 5.5, 7 Hz)

EXAMPLE 17

2,3-Difluoro-6-nitro-}[(R)-(2-p-toluenesulfonyloxypropyl)]oxy}benzene (XIR, Xa=Xb=F, Rd=Ts)

According to the tosylating method as described in Example 8, 6.74 g of the titled compound was obtained from 4.62 g of the compound obtained in Example 16, 4.53 g of p-toluenesulfonyl chloride and 12 ml of pyridine.

m.p.: 67.5°–68° C.

$^1$H-NMR (CDCl$_3$)δ: 1.43 (3H, d, J=6 Hz), 2.41 (3H, s), 4.08–4.40 (2H, m), 4.76–5.08 (1H, m), 7.04 (1H, ddd, J=7, 9, 9.5 Hz), 7.67 (1H, ddd, J=2.5, 5.5, 7 Hz), 7.32, 7.80 (2H each, d each, J=8.5 Hz)

EXAMPLE 18

2,3-Difluoro-6-amino-{[(R)-(2-p-toluenesulfonyloxypropyl)]oxy}benzene (XIIR, Xa=Xb=F, Rd=Ts)

To a solution of 581 mg of the compound obtained in Example 17 in 20 ml of ethanol was added 200 mg of 5% palladium on charcoal. Catalytic reduction was performed under atmospheric pressure at room temperature. After the theoretical amount of hydrogen was absorbed, the catalyst was removed by filtration, and the solvent was removed under reduced pressure. The residue was purified through silica gel column chromatography to yield 520 mg of the titled compound.
m.p.: 37°-38° C.
$^1$H-NMR (CDCl$_3$) δ: 1.34 (3H, d, J=6.5 Hz), 2.44 (3H, s), 3.50 (2H, br s), 4.02-4.14 (2H, m), 4.80-5.14 (1H, m), 6.38 (1H, ddd, J=2.5, 5.5, 7 Hz), 6.71 (1H, ddd, i=7, 9, 9.5 Hz), 7.32, 7.80 (2H each, d each, J=8.5 Hz)

REFERENCE EXAMPLE D-3

(S)-(-)-7,8-Difluoro-3-methyl-3,4-dihydro-2H-[1,4]benzoxazine (XIVS, Xa=Xb=F)

According to the methods of Example 18 and Reference Example D-1, 262 mg of the titled compound was obtained from 775 mg of 2,3-difluoro-6-nitro([(R)-(2-p-toluenesulfonyloxypropyl)]oxy}benzene (XIR, Xa=Xb=F, Rd=Ts). The physical data of the product were identical to those of the authentic specimen obtained as described in *Argic. Biol. Chem.*, 51, (5), 1265-1270 (1987) and EP-A-0,206,283.

EXAMPLE 19

2,3-Difluoro-6-amino-}[(R)-2-(tetrahydropyran-2-yl)oxypropyl]oxy}benzene VIR, Xa=Xb=F, Rc=THP)

To a solution of 476 mg of 2,3-difluoro-6-nitro{[(R)-2-tetrahydropyran-2-yl)oxypropyl]oxy}benzene (IR, Xa=Xb=F, Rc=THP) in 20 ml of ethanol was added 200 mg of 5% palladium on charcoal. Catalytic reduction was performed under atmospheric pressure at room temperature. After the theoretical amount of hydrogen was absorbed, the catalyst was received by filtration and, from the filtrate, the solvent was removed under reduced pressure. The residue was purified through silica gel colurdn chromatography to yield 385 mg of the oily titled compound as a mixture of the diastereomers.
$^1$H-NMR (CDCl$_3$) 67 : 1.23, 1.33 (3H totally, d each, J=6 Hz), 1.36-1.98 (6H, m), 3.36-4.32 (5H, m), 4.70-4.90 (1H, m), 6.39 (1H, ddd, J=2.5, 5.5, 7 Hz), 7.72 (1H, ddd, J=7, 9, 9.5 Hz)

EXAMPLE 20

2,3-Difluoro-6-(2,2-diethoxycarbonylethenyl)amino-}[(R)-2-hydroxypropyl]oxy}benzene (XR, Xa=Xb=F, R=Et)

2,3-Difluoro-6-amino{[(R)-2-(tetrahydropyran-2-yl)propyl]oxy}benzene (VIR, Xa=Xb=F, Rc=THP) obtained from 6.35 g of 2,3-difluoro-6-nitro}[(R)-2-(tetrahydropyran-2-yl)oxypropyl]oxy}benzene (IR, Xa=Xb =F, Rc=THP) according to the method as described in Example 19 and 4.37 g of EMME was heated at 150° C. with stirring under atmospheric pressure for 1.5 hours. Then, the mixture was further heated at the same temperature under reduced pressure for 30 minutes. To the mixture was added 60 ml of anhydrous ethanol and 640 mg of pyridinium tosylate, and the mixture was stirred at room temperature overnight. The solvent was removed under reduced pressure, and the residue was dissolved in ethyl acetate. This solution was washed sequentially with 1 N hydrochloric acid, saturated sodium bicarbonate aqueous solution and saturated sodium chloride aqueous solution, and dried over anhydrous magnesium sulfate. The solvent was removed under reduced pressure. The residue was purified through silica gel column chromatography to yield 5.56 g of the titled compound.
m.p.: 88°-90° C.
$^1$H-NMR (CDCl$_3$) δ: 1.25-1.45 (9H, m), 3.54 (1H, d, J=4.5 Hz), 3.86-4.46 (7H, m), 6.76-7.10 (2H, m), 8.49 (1H, d, J=14.5 Hz)

REFERENCE EXAMPLE B-2

(S)-Diethyl (7,8-difluoro-3-methyl-3,4-dihydro-2H-[1,4]-benzoxazine-4-yl)methylenemalonate (XVS, Xa=Xb=F, R=Et)

According to the method as described in Reference Example B-1, 560 mg of the compound obtained in Example 20 was cyclized in the presence of 1.3 molar equivalent amount of Mitsunobu Reagent. The titled compound was obtained in quantitative yield.
$^1$H-NMR (CDCl$_3$) δ: 1.22-1.42 (9H, m), 3.90-4.44 (7H, m), 6.74-6.88 (2H, m), 7.78 (1H, s)

EXAMPLE 21

2,3-Difluoro-6-(2,2-diethoxycarbonylethenyl)amino-{[(R)-2-p-toluenesulfonyloxypropyl]oxy}benzene (XIIIR, Xa=Xb=F, Rd=Ts, R=Et)

Tosylation reaction was carried out according to the method as described in Example 4, and 3.2 g of the titled compound was obtained from 2.43 g of the compound obtained in Example 20, 4.5 ml of pyridine and 1.49 g of p-toluenesulfonyl chloride.
m.p.: 68°-69° C.
$^1$H-NMR (CDCl$_3$) δ: 1.33, 1.36 (3H each, t each, J=7 Hz), 1.50 (3H, d, J=7 Hz), 2.40 (3H, s), 4.02-4.42 (6H, M), 4.96 (1H, sixtet-like), 6.85-7.00 (2H, m), 7.28, 7.79 (2H each, d each, J=9 Hz), 8.37 (1H, d. J=14 Hz)

REFERENCE EXAMPLE C-3

(S)-Diethyl (7,8-difluoro-3-methyl-3,4-dihydro-2H-[1,4]-benzoxazine-4-yl)methylenemalonate (XVS, Xa=Xb=F, R=Et)

The oily titled compound was obtained in quantitative yield by the cyclization reaction according to the method as described in Reference Example C-1 from 791 mg of the compound obtained in Example 21, 207 mg of potassium carbonate and catalytic amount of 18-crown-6-ether.

EXAMPLE 22

2,3-Difluoro-6-amino-{[(R)-2-hydroxypropyl]oxy}benzene (IXR, Xa=Xb=F)

To a solution of 3.1 g of 2,3-difluoro-6-nitro-{[(R)-2-hydroxypropyl]oxy}benzene (VIIIR, Xa=Xb=F) in 50 ml of ethanol was added 500 mg of 5% palladium on charcoal. Catalytic reduction was performed under atmospheric pressure at room temperature. When the absorption of hydrogen ceased, the catalyst was removed by filtration and the solvent was removed from the filtrate under reduced pressure. The residue was purified through silica gel column chromatography to yield 2.47 g of the titled compound.

m.p.: 47°–48° C.

$^1$H-NMR (CDCl$_3$) δ: 1.21 (3H, d, J=6.5 Hz), 3.25–4.30 6H, M), 6.43 (1H, ddd, J=2.5, 5.5, 7 Hz), 7.76 (1H, ddd, J 7, 9, 9.5 Hz)

EXAMPLE 23

2,3-Difluoro-6-(2,2-dimethoxycarbonylethenyl)amino-{[(R)-2-hydroxypropyl]oxy}benzene (XR, Xa=Xb=F, R=Me)

According to the method as described in Example 6, 11.32 g of the titled compound was obtained from 9.30 g of the compound obtained in Example 16.

m.p.: 104°–105° C.

$^1$H-NMR (CDCl$_3$) δ: 1.28 (3H, d, J=6.5 Hz), 3.44 (1H, d, J=4.5 Hz), 3.79, 3.87 (3H each, s each), 6.76–7.11 (2H, m), 8.52 (1H, J=14.5 Hz)

EXAMPLE 24

2,3-Difluoro-6-(2,2-dimethoxycarbonylethenyl)amino-[(R)-2-(p-toluenesulfonyloxypropyl)oxy]benzene (XIIIR, Xa=Xb=F, Rd=Ts, R=Me)

According to the method as described in Example 4, 13.52 g of the titled compound was obtained from 0.36 g of the compound obtained in Example 23.

m.p.: 92°–93° C. $^1$H-NMR (CDCl$_3$) δ: 1.51 (3H, d, J=6.5 Hz), 2.41 (3H, s), 3.82, 3.88 (3H each, s each), 4.07–4.44 (2H, m), 4.83–5.16 (1H, m), 6.80–7.15 (2H, m), 7.32, 7.85 (2H each, d each, J=8 Hz), 8.46 (1H, d, J=14.5 Hz)

REFERENCE EXAMPLE C-4

(S)-Dimethyl (7,8-difluoro-3-methyl-3,4-dihydro-2H-[1,4]-benzoxazine-4-yl)methylenemalonate (XVS, Xa=Xb=F, R=Me)

According to the method as described in Reference Example C-1, 3.12 g of the titled compound was obtained from 4.99 g of the compound obtained in Example 24.

m.p.: 108°–109° C.

$^1$H-NMR (CDCl$_3$) δ: 1.32 (3H, d, J=7 Hz), 3.81, 3.85 (3H each, s each), 3.94–4.63 (3H, m), 6.80 (2H, q-like), 7.82 (1H, s)

EXAMPLE 25

2,3-Difluoro-6-nitro-[(2-hydroxypropyl)oxy]benzene (VIII, Xa=Xb=F)

To an ice-cooled suspension of 207 mg of sodium hydride (60%), which was washed with anhydrous solvent to remove the mineral oil, in 4 ml of anhydrous toluene was added dropwise a solution of 793 mg of 2-O-tetrahydropyranylpropane-1,2-diol (III, Rc=THP) in 3 ml of anhydrous toluene, and the mixture was stirred at the same temperature for 30 minutes. To the mixture were added dropwise a solution of 797 mg of 2,3,4-trifluoronitrobenzene (II, Xa=Xb=Xc=F) in 3 ml of anhydrous toluene with stirring under cooling with ice. The mixture was stirred at an external temperature of 5° C. for 24 hours. To the mixture were added water and ethyl acetate, and the resulting mixture was shaken. The organic layer was separated and dried over anhydrous magnesium sulfate. The solvent was removed under reduced pressure to yield 2,3-difluoro-6-nitro-([2-(tetrahydropyran-2-yl)oxypropyl]oxy}benzene (I, Xa=Xb=F, Rc =THP) in quantitative yield. This compound was dissolved in 13.5 ml of anhydrous ethanol and to this solution was added 145 mg of Pyridinium tosylate. The mixture was stirred at room temperature for 24 hours and then heated under refluxing for 1 hour. The solvent was removed under reduced pressure and the residue was dissolved in ethyl acetate. This solution was washed with 1 N hydrochloric acid, a 5% sodium bicarbonate aqueous solution and water, then dried over anhydrous sodium sulfate. The solvent was removed under reduced pressure. The residue was purified through silica gel column chromatography to yield 902 mg of the oily titled compound.

$^1$H-NMR (CDCl$_3$) δ: 1.25 (3H, d, J=6 Hz), 3.00 (1H, br d, J=2.5 Hz), 3.99–4.43 (3H, m), 7.03 (1H, ddd, J=7, 9, 9.5 Hz), 7.74 (1H, ddd, J 2.5, 5.5, 7 Hz)

EXAMPLE 26

2,3-Difluoro-6-nitro-{[(R)-2-hydroxypropyl]oxy}benzene (VIIIR, Xa=Xb=F)

To an ice-cooled suspension of 720 mg of sodium hydride (60%) in 12 ml of anhydrous toluene was added dropwise a solution of 2.88 g of 2-0-tetrahydropyranyl-(R)-propane-1,2-diol (IIIR, Rc=THP) in 12 ml of anhydrous toluene, and the mixture was stirred at the same temperature for 30 minutes and at room temperature for 10 minutes. The mixture was added dropwise to a solution of 2.66 g of 2,3,4-trifluoronitrobenzene in 12 ml of anhydrous toluene with stirring under cooling with ice. The mixture was stirred at an external temperature of 5° C. for 24 hours. To the mixture were added ice-water and benzene, and the resulting mixture was shaken. The organic layer was separated and dried over anhydrous magnesium sulfate. The solvent was removed under reduced pressure to yield 2,3-difluoro-6-nitro-{[(R)-2-(tetrahydropyran-2-yl)oxypropyl]oxy}benzene (IR, Xa=Xb=F, Rc=THP) in quantitative yield. This compound was dissolved in 38 ml of anhydrous ethanol and to this was added 450 mg of pyridinium tosylate. The mixture was heated under refluxing for 1 hour. The solvent was removed under reduced pressure, and the residue was dissolved in ethyl acetate. This solution was washed successively with 1 N hydrochloric acid, a 5% sodium bicarbonate aqueous solution and water, then dried over anhydrous sodium sulfate. The solvent was removed under reduced pressure. The residue was purified through silica gel column chromatography to yield 3.20 g of the oily titled compound.

$^1$H-NMR (CDCl$_3$) δ: 1.26 (3H, d, J=6 Hz), 2.89 (1H, br-d, J=2.5 Hz), 3.95–4.46 (3H, m), 7.03 (1H, d-d-d, J=7, 9, 9.5 Hz), 7.75 (1H, d-d-d, J=2.5, 5.5, 7 Hz)

EXAMPLE 27

2,3-Difluoro-6-nitro-{[(S)-2-hydroxypropyl]oxy}benzene (VIIIS, Xa=Xb=F)

According to the method as described in Example 26, 3.03 g of the oily titled compound was obtained from 2.88 g of 2-O-tetrahydropyranyl-(S)-propane-1,2-diol (IIIS, Rc=THP) and 2.66 g of 2,3,4-trifluoronitrobenzene (II, Xa=Xb=Xc=F).

$^1$H-NMR (CDCl$_3$) 67 : 1.26 (3H, d, J=6 Hz), 2.88 (1H, d, J=2.5 Hz), 3.96–4.44 (3H, m), 7.03 (1H, d-d-d, J=7, 9, 9.5 Hz), 7.75 (1H, d-d-d, J=2.5, 5.5, 7 Hz)

The products obtained in Examples 26 and 27 were confirmed by high performance liquid chromatography (HPLC) method that no isomerization had occurred. The products were converted to the 3,5-dinitrobenzoyl derivatives by reacting with 3,5-dinitrobenzoyl chloride and pyridine. The resulting 3,5-dinitrobenzoyl derivatives were subjected to HPLC to determine optical purity. The HPLC column used was CHIRALSEL OD column available from DAISEL CHEMICAL INDUSTRIES LTD.

REFERENCE EXAMPLE A-4

(1) (R)-Methyl-O-(tetrahydropyran-2-yl)lactate

A mixture of 156.15 g of (R)-(+)-methyl lactate, 151.42 g of 2,3-dihydropyran, 17.42 g of dl-camphor-10-sulfonic acid and 150 ml of anhydrous 1,2-dichloroethane was stirred under cooling with ice overnight. To the mixture was added 900 ml of 1,2-dichloroethane, and the resulting mixture was washed with a saturated sodium bicarbonate aqueous solution and water. The organic layer was dried over anhydrous magnesium sulfate. The solvent was removed under reduced pressure to yield the oily titled compound in quantitative yield.

(2) 2-O-(Tetrahydropyran-2-yl)-(R)-propan-1,2-diol (IIIR, Rb=THP)

To a suspension of 85.12 g o-@sodium borohydride in 750 ml of 1,2-dichloroethane, a solution of the total amount of the compound obtained in Reference Example A-4 (1) in 243 ml of methanol was added dropwise, while the inner temperature was kept below 30° C. Then, 122 ml of methanol was added at the same temperature. The mixture was stirred at room temperature for 1 hour. To the mixture was added 2200 ml of water and the organic layer was separated. The aqueous layer was extracted with 1,2-dichloroethane. The combined organic layer was washed with a saturated sodium chloride aqueous solution and then dried over anhydrous magnesium sulfate. The solvent was removed under reduced pressure, and the residue was distilled under reduced pressure to yield 174 g of the titled compound. The physical data of the products obtained in this Reference Example A-4 were identical to those of the products obtained in Reference Example A-3 (2).

While the invention has been described in detail and with reference to specific embodiments thereof, it will be apparent to one skilled in the art that various changes and modifications can be made therein without departing from the spirit and scope thereof.

What is claimed is:

1. A propoxybenzene derivative represented by the following formula:

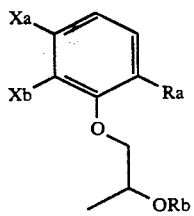

wherein Ra represents a nitro group, an amino group which may have a protecting group or an —NHCH=C(COO—$C_{1-6}$-Alkyl)$_2$ group, Rb represents a hydrogen atom, a protecting group for the hydroxyl group or a p-toluenesulfonyl, methanesulfonyl or trifluoromethanesulfonyl group and Xa and Xb, which may be the same or different, each represents a halogen atom.

2. 2,3-Difluoro-6-nitro-[(2-hydroxypropyl)oxy]benzene according to claim 1.

* * * * *